(12) United States Patent
Giacomoni et al.

(10) Patent No.: US 7,794,694 B2
(45) Date of Patent: Sep. 14, 2010

(54) COSMETIC COMPOSITIONS AND METHODS CONTAINING A TANNING AGENT AND LIPOSOME ENCAPSULATED URSOLIC ACID

(75) Inventors: Paolo Ulderico Giacomoni, Commack, NY (US); Abul M. Manirazman, Port Jefferson, NY (US)

(73) Assignee: E-L Management Corp., New York, NY (US)

( * ) Notice: Subject to any disclaimer, the term of this patent is extended or adjusted under 35 U.S.C. 154(b) by 820 days.

(21) Appl. No.: 11/167,389

(22) Filed: Jun. 27, 2005

(65) Prior Publication Data

US 2006/0002870 A1  Jan. 5, 2006

Related U.S. Application Data

(60) Provisional application No. 60/584,749, filed on Jul. 1, 2004.

(51) Int. Cl.
*A61Q 17/04* (2006.01)
*A61K 8/00* (2006.01)
*A61K 8/18* (2006.01)

(52) U.S. Cl. ..................... 424/59; 424/401; 424/450

(58) Field of Classification Search .................. 424/401
See application file for complete search history.

(56) References Cited

U.S. PATENT DOCUMENTS

| | | | |
|---|---|---|---|
| 4,529,561 A | 7/1985 | Hunt et al. | |
| 4,572,425 A | 2/1986 | Russell | |
| 5,229,104 A * | 7/1993 | Sottery et al. | 424/59 |
| 5,458,872 A * | 10/1995 | Durand | 424/59 |
| 5,942,212 A | 8/1999 | Lentini et al. | |
| 6,007,796 A | 12/1999 | Menzel et al. | |
| 6,231,837 B1 * | 5/2001 | Stroud et al. | 424/59 |
| 6,482,397 B1 | 11/2002 | Scott et al. | |
| 6,982,284 B1 * | 1/2006 | Brown et al. | 514/577 |
| 2003/0129211 A9 * | 7/2003 | Livoreil et al. | 424/401 |
| 2004/0042979 A1 | 3/2004 | Sokolinsky et al. | |
| 2004/0180082 A1 | 9/2004 | Kang et al. | |
| 2005/0003024 A1 | 1/2005 | Oblong et al. | |

FOREIGN PATENT DOCUMENTS

| | | |
|---|---|---|
| DE | 19857010 | 6/2000 |
| EP | 0424282 | 4/1991 |
| JP | 2002-087926 | 3/2002 |
| JP | 2002-363557 | 12/2002 |
| KR | 2003026414 A | 4/2003 |

(Continued)

OTHER PUBLICATIONS

PCT International Search Report; International Application No. PCT/US05/022650; Completion Date: Mar. 1, 2006; Date of Mailing: May 3, 2006.

(Continued)

*Primary Examiner*—Johann R Richter
*Assistant Examiner*—Danielle Sullivan
(74) *Attorney, Agent, or Firm*—Radha Masilamani; Peter Giancana

(57) ABSTRACT

A composition for topical application to the skin to provide tanning, comprising a liposome encapsulated ursolic acid, a tanning agent and a cosmetically acceptable carrier, and methods of use thereof.

14 Claims, 9 Drawing Sheets

FOREIGN PATENT DOCUMENTS

WO    WO 01/74327 A1    10/2001

OTHER PUBLICATIONS

PCT Written Opinion of the International Searching Authority, or the Declaration; International Application No. PCT/US05/022650; Completion Date: Mar. 1, 2006; Mailing Date: May 1, 2006.

"Pharmacology of Oleanic Acid and Ursolic Acid", Journal of Ethnopharmacology, p. 45, 57-58, 1995.

Brown, Goodtzova, Yarosh, Both; "Liposome-encapsulated Ursolic Acid Increases Ceramides and Collagen in Human Skin Cell", Arch Dermatol Res(2002), vol. 293; pp. 570-571.

"What are liposomes?" Laboratory of Liposomal Research Nov. 18, 2003.

Yarosh & Brown; "Building a Better Barrier from the Inside Out"; Cosmetics & Tolietries magazine, Nov. 2003; vol. 118 pp. 47-51 Allured Publishing Corp.

* cited by examiner

Legend
1. 3% DHA + pentylene glycol (control)
2. 3% DHA + pentylene glycol + empty liposome
3. 3% DHA + pentylene glycol + 0.05% ursolic acid
4. 3% DHA + pentylene glycol + oleonoline DPG (olive leaf ext.)
5. 3% DHA + 5% pentylene glycol + empty liposome + 0.05% ursolic acid
6. 3 % DHA + 5% pentylene glycol + 3% Merosphere
7. 7 % DHA Legend
1. 3% DHA + pentylene glycol (control)
2. 3% DHA + pentylene glycol + empty liposome
3. 3% DHA + pentylene glycol + 0.05% ursolic acid
4. 3% DHA + pentylene glycol + oleonoline DPG (olive leaf ext.)
5. 3% DHA + 5% pentylene glycol + empty liposome + 0.05% ursolic acid
6. 3 % DHA + 5% pentylene glycol + 3% Mcrosphcre
7. 7 % DHA Legend
1. 3% DHA + pentylene glycol (control)
2. 3% DHA + pentylene glycol + empty liposome
3. 3% DHA + pentylene glycol + 0.05% ursolic acid
4. 3% DHA + pentylene glycol + oleonoline DPG (olive leaf ext.)
5. 3% DHA + 5% pentylene glycol + empty liposome + 0.05% ursolic acid
6. 3 % DHA + 5% pentylene glycol + 3% Merosphere
7. 7 % DHA

COSMETIC COMPOSITIONS AND METHODS CONTAINING A TANNING AGENT AND LIPOSOME ENCAPSULATED URSOLIC ACID

The following invention claims priority under 35 USC 119e of U.S. provisional application 60/584,749 filed Jul. 1, 2004.

1. Field of the Invention

The present invention relates to skin care cosmetic compositions and methods. In particular, the present invention relates to novel cosmetic compositions and methods comprising the novel combination of a tanning agent such as dihydroxy acetone (DHA) and liposome encapsulated ursolic acid.

2. Background of the Invention

A tan is often considered a sign of physical health and social success. A tan can be achieved naturally by exposing one's skin to solar or artificial ultraviolet radiation, or by the use of self-tanning products. However, a tan generated by exposure to ultraviolet radiation is undesirable because of the known adverse effects of prolonged exposure to such UV-A radiation.

It is presently known in the art to use dihydroxy acetone (DHA) as a non-UV induced tanning aid. For many years in its infancy, DHA-induced tanning was characterized by an unnatural-looking orange color. Even with recent improvements, some consumer find that their use of DHA produces a less than natural-looking tan. Further, DHA may take several hours to effect a color change in the skin. Specifically, with many self-tanners, it can take three to five hours for the coloration to be revealed, which for the busy consumer, may be an undesirably long waiting period.

There is thus an increasing demand for fast-acting self-tanning products which give a coloration closer to that of a natural tan.

SUMMARY OF THE INVENTION

Figure 1:
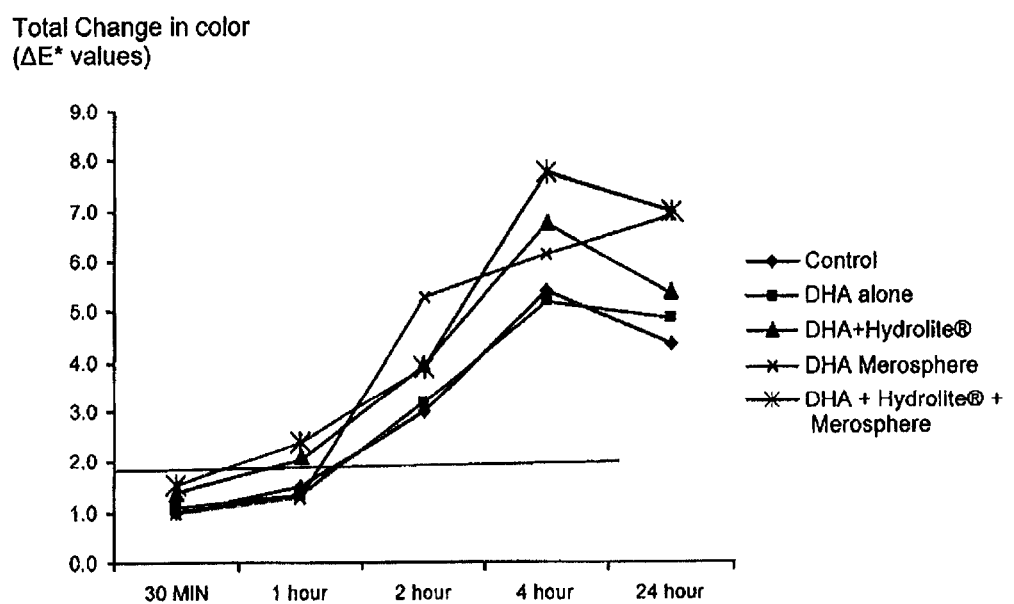
FIG. 1 Graphical depiction of the Effect of Ursolic Acid in Merospheres and Hydrolite® on improving DHA induced self-tanning.

The present invention provides a composition for topical application to the skin to provide tanning comprising a liposome encapsulated ursolic acid, a tanning agent and a cosmetically acceptable carrier.

The present invention further provides a method of tanning comprising topically applying to the skin, a composition comprising a liposome encapsulated ursolic acid, dihydroxyacetone and a cosmetically acceptable carrier.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

Ursolic acid is a nontoxic, naturally-occurring triterpenoid that is found in a variety of plants with medicinal properties. Studies have shown that ursolic acid has both antiinflammatory, antitumor and antiaging properties. See "*Pharmacology of Oleanonic Acid and Ursolic Acid*," Journal of Ethnopharmacology, 49, 57-58, 1995. Ursolic acid, however, is difficult to solubilize. For example, ursolic acid dissolved in ethanol or other alcohols come out of solution when applied to cultured cells. Moreover, ursolic acid can exhibit poor penetration in human skin when incorporated into a common solvent. See "Liposome-encapsulated ursolic acid increases in ceramides and collagen in human skin cells," by Dawn M. Both, Karina Goodtzova, Daniel B. Yarosh, and David A. Brown, Arch Dermatol Res, 2002, 293: 570-571. As one method of delivering ursolic acid into the skin, ursolic acid is incorporated into vesicles that enhance the ability of ursolic acid in penetrating into the skin.

Liposomes are the smallest artificial vesicles of spherical shape that can be produced from natural non-toxic phospholipids and cholesterol. See "What are Liposomes," Laboratory of Liposomal Research, Nov. 18, 2003. Liposomes have been used as vesicles for carrying a great variety of molecules, such as small drug molecules, proteins, nucleotides and plasmids. Liposomes are extremely versatile and due to the variability of their composition, they can be used for a large number of applications, including delivery of actives into the skin in cosmetic applications. It has been found that liposome based formulations do not disturb the integrity of the skin lipid bilayers and are not washed out while cleaning the skin.

As a result of attempts to protect ursolic acid in vesicles, recent studies have shown that liposome-encapsulated ursolic acid ("URA liposome") overcome the solubilizing difficulties discussed hereinabove. Moreover, URA liposomes have been shown to provide anti-aging benefits through increase of ceramide and collagen content in human skin cells, as well as antiinflammatory and antitumor properties. See "Liposome-encapsulated ursolic acid increases in ceramides and collagen in human skin cells," by Dawn M. Both, Karina Goodtzova, Daniel B. Yarosh, and David A. Brown, Arch Dermatol Res, 2002, 293: 569-575.

The present invention is predicated on the surprising observation that dihydroxyacetone ("DHA") in combination with at least one URA liposome provides an unexpectedly rapid and relatively natural-looking darkening/tanning of human skin. While not wishing to be bound by any theories, it is believed that because the URA liposome is better able to penetrate the skin, the URA liposome opens a pathway for the DHA to also better penetrate the skin to provide a more pronounced and rapid darkening/tanning of the skin. Specifically, as has been discussed hereinabove, it is believed that URA is difficult to solubilize for penetration into the skin, and therefore the liposomes provide the vesicle for carrying the URA into the skin. Upon opening a pathway into the skin, the DHA of the inventive composition comprising the combination of DHA and URA liposomes can readily follow the pathway into the skin.

To formulate the URA liposome of the present invention, any liposomes known to those skilled in the art may be used. Liposomes of the present invention can be formed from a variety of phospholipids, such as cholesterol, stearylamine, or phosphatidylcholines. Lipids from egg yolks or soybeans can also be used to make liposomes. Conventional liposome preparation methods include a number of steps in which multi- or the bilayer-forming components (phospholipids or mixtures of phospholipids with other lipids e.g. cholesterol) are dissolved in a volatile organic solvent or solvent mixture in a flask followed by evaporation of the solvent under conditions such as temperature and pressure which will prevent phase separation. Upon solvent removal, a dry lipid mixture, usually in the form of a film deposit on the walls of the reactor, is hydrated with an aqueous medium which may contain dissolved buffers, salts, conditioning agents and an active substance to be entrapped. Liposomes will form in the hydration step whereby a proportion of the aqueous medium becomes encapsulated in the liposomes. The hydration can be performed with or without energizing the solution by means of stirring, sonication or microfluidisation with subsequent extrusion through one or more polycarbonate filters. The free non-encapsulated active substance can be separated for recovery and the product is filtered, sterilized, optionally lyophilized, and packed. Other methods of making liposomes involve injection of an organic solutions of lipids into an aqueous medium with continuous removal of solvent, use of spray drying, lyophilization, microemulsification and microfluidization. See U.S. Pat. Nos. 4,529,561 and 4,572,425.

In the present invention, for incorporation into the liposome, ursolic acid as an active ingredient can be in an isolated form or provided as a pure/semi-pure form of an extract. More specifically, ursolic acid may be derived from a plant, as for example from a plant part or as a solvent extract. Ursolic acid may be found in a variety of plants, including but not limited to, *Calluna vulgaris* (Ericaceae), *Eribotrya japonica* (Rosaceae), *Eucalyptus hybrid* (Myrtaceae), *Melaleuca leucadendron* L. (Myrtaceae), *Glechoma hederacea* L. (Labiatae), *Ocimum sanctum* (Labiatae), *Rosmarinus officinalis* L. (Labiatae), *Pyrola rotundifolia* (Pyrolaceae), *Psychotria serpens* L. (Rubiaceae), *Sambucus chinesis* Lindl (Caprifoliaceae), *Solanum incanum* L. (Solanaceae), and *Tripterospermum taiwanense* (Gentianaceae). It should be understood that other analogues or homologs of ursolic acid that have similar biological properties may also be used, such as oleanolic acid, which is an isomer of ursolic acid. The skilled artisan is readily capable of determining the efficacy of such analogs or homologs by following the protocol in the examples provided herein to determine the ability to enhance DHA activity, thereby enhancing tanning of the skin.

The concentrations of the active ursolic acid may vary from source to source, so as a guideline, it is recommended to use the amount of extract that would provide an equivalent concentration of isolated ursolic acid in a range of from 0.0001 to 5%. In addition, as shown in the examples below, although ursolic acid is the principle active component in achieving tanning, additional components, although not necessarily very effective on their own, may be present in the plant extracts that can have some contributory activity.

The liposome encapsulation is carried out by methods well known in the art. In the preferred embodiment, phosphatidylcholine and cholesterol are dissolved in ethanol at a 2:5:1 molar ratio. This solution is split into aliquots, and a range of concentrations of ursolic acid are added so that the loading capacity of liposomes can be determined. One aliquot receives no ursolic acid to provide an empty liposome control. Each aliquot is injected through a 30G1/2 needle into an equal volume of cold 1× phosphate-buffered saline (PBS). The resulting liposomes are analyzed by high-performance thin-layer chromatography (HPTLC) to determine the concentration of ursolic acid incorporated into the liposomes. Encapsulated liposomes may be obtained, for example, under the trade name Merospheres, from Barnet Products Corporation in Englewood Cliffs, N.J.

In the present invention, the final concentration of ursolic acid in the liposomes used is between 0.001% to 0.9%, preferably from 0.005% to 0.5% and most preferably from 0.01% to 0.1%. The concentration of ursolic acid in the final composition is between 0.0001 to 0.1%, preferably from 0.0002 to 0.005%, and most preferably from 0.0002 to 0.0003%.

In the present invention, the inventive composition further comprises a tanning agent.

Although any tanning agent known to those skilled in the art are within the scope of this invention, preferably dihydroxyacetone (DHA) is used. DHA is a known skin darkening agent.

However, as discussed above, the use of DHA for skin tanning purposes produces what may be perceived by some as an unnatural-looking sun tan. Further, DHA may take several hours to effect a color change in the skin. The inventive combination of DHA with URA liposomes beneficially provides a more natural looking tan at a more rapid rate because it is believed that the penetrative effectiveness of URA liposomes provide a pathway for DHA to more readily penetrate the skin.

It should be noted that other tanning agents are also contemplated to be within the scope of this invention. For example, tanning agents including but not limited to isatin, alloxan, ninhydrin, glyceraldehyde, mesotartaric aldehyde, glutaraldehyde, erythrulose, pyrazoline-4,5-dione derivatives, and 4,4-dihydroxypyrazoline-5 and derivatives thereof may used as an alternative or in conjunction with DHA.

In the preferred embodiment, DHA is used in an amount of from 0.001% to 10%, preferably from 0.01% to 5% and most preferably from 0.1% to 3%.

The DHA or tanning agent may alternatively be encapsulated in a liposome to enhance delivery of the DHA or tanning agent into the skin. The method of encapsulation may be as described hereinabove, or by any other known means of encapsulation.

The preferred embodiment of the present invention may also contain a penetration enhancer to facilitate penetration of the composition comprising the combination of DHA and URA liposomes. Suitable penetration enhancers include but are not limited to pentylene glycol, C12-15 Alkyl Benzoate, polysorbate-polyethylenesorbitan-monolaurate (Tween-20®), polyethylene glycol, ethoxydiglycol, dimethylsulfoxide, sodium lauryl sulfate, lecithin and mixtures thereof.

The penetration enhancer is preferably used in an amount of from 0.001% to 10%, preferably from 0.01% to 8%, and most preferably from 0.1% to 5% by weight of the composition.

The composition optionally further comprises a cosmetically acceptable vehicle that is suitable for topical application to skin, hair and/or nails. Cosmetically acceptable vehicles are well known in the art and are selected based on the end use of the application. For example, vehicles of the present invention include, but are not limited to, those suitable for application to the skin. Such vehicles are well known to those of ordinary skill in the art, and can include one or more compatible liquid or solid filler diluents or vehicles which are suitable for application to the skin. The exact amount of vehicle will depend upon the level of any other optional ingredients that one of ordinary skill in the art would classify as distinct from the vehicle (e.g., other active components). The compositions of the present invention preferably comprise from about 75% to about 99.99%, more preferably from about 85% to about 99.99%, and most preferably from about 93% to about 98%, by weight of the composition, of a vehicle.

The vehicle and the compositions herein can be formulated in a number of ways, including but not limited to emulsions. For example, suitable emulsions include oil-in-water, water-in-oil, water-in-oil-in-water, oil-in-water-in-oil, and oil-in-water-in-silicone emulsions. Preferred compositions comprise an oil-in-water emulsion.

The compositions of the present invention can be formulated into a wide variety of product types, including creams, waxes, pastes, lotions, milks, mousses, gels, oils, tonics and sprays. Preferred compositions are formulated into lotions, creams, gels, and sprays. These product forms may be used for a number of applications, including but not limited to, hand and body lotions, facial moisturizers, topical analgesics and make-ups/cosmetics. Any additional components required to formulate such products vary with product type and can be routinely chosen by one skilled in the art.

Other Components

The formulation also can comprise other components that may be chosen depending on the carrier and/or the intended use of the formulation. It should be noted that a person of ordinary skill in the art is capable of determining the amounts of additional components that would be suitable for each formulation through routine experimentation. Additional components include, but are not limited to antioxidants (such as BHT); chelating agents (such as disodium EDTA); emulsion stabilizers (such as carbomer); preservatives (such as methyl paraben); fragrances (such as pinene); flavoring agents (such as sorbitol); humectants (such as glycerine); waterproofing agents (such as PVP/Eicosene copolymer); water soluble film-formers (such as hydroxypropyl methylcellulose); oil-soluble film formers (such as hydrogenated C-9 Resin); moisturizing agents (such as cholesterol); cationic polymers (such as Polyquatenium 10); anionic polymers (such as xanthan gum); vitamins (such as tocopherol); sunscreens (such as octyl methoxycinnamate, titanium dioxide, zinc oxide, camphor derivatives, cinnamates, salicylates, benzophenones, triazines, PABA derivatives, diphenylacrylate derivatives, and dibenzoylmethane derivatives) and the like. Preferred additional components in the present invention include bronzers or other colorants that provide either an immediate tanned look, and/or provide the user with an indication of where the product has been applied so as to avoid streaking. Additionally preferred components include DHA-enhancing ingredients such as lactic acid, sugars, and film-forming agents.

The compositions can also encompass one or more additional active components, and as such can be either cosmetic or pharmaceutical compositions in addition to tanning and concentrations may be determined by one skilled in the art to determine effectiveness of product as discussed in the present invention. Examples of useful actives include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antihyperkeratolytic agents, anti-dry skin agents, antiperspirants, antipsoriatic agents, antiseborrheic agents, antiaging agents, antiwrinkle agents, antiasthmatic agents and bronchodilators, antihistamine agents, wound-healing agents, vitamins, corticosteroids, additional tanning agents or hormones. More specific examples of useful active agents include retinoids such as retinol, and esters, acids, and aldehydes thereof; ascorbic acid, and esters and metal salts thereof, tocopherol and esters and amide derivatives thereof; shark cartilage; milk proteins; alpha- or beta-hydroxy acids; DHEA and derivatives thereof; topical cardiovascular agents; clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, hydrocortisone, hydrocortisone 21-acetate, hydrocortisone 17-valerate, hydrocortisone 17-butyrate, betamethasone valerate, betamethasone dipropionate, triaminolone acetonide, fluocinonide, clobetasol, proprionate, benzoyl peroxide, crotamiton, propranol, promethazine, and mixtures thereof.

Particularly preferred embodiments of the present formulations are skin care lotions or creams used as a self-tanning product. The present formulations may therefore be combined with additional aesthetic agents such as moisturizers, emollients or humectants. Examples of useful combinations are oils, fats, waxes, esters, fatty acid alcohols, fatty acid ethoxylates, glycols, sugars, hyaluronic acid and hyaluronates, dimethicone, cyclomethicone, and the like. Further examples can be found in the International Cosmetic Ingredient Dictionary, CTFA, Ninth Edition, 2003.

Method of Tanning the Skin

The present inventive compositions are particularly useful as products useful as methods of tanning the skin through the inventive combination of DHA and URA liposomes.

Such methods comprise administering or topically applying to the skin a safe and effective amount of the composition of the present invention. The amounts of the components in the compositions will vary depending upon the level of tanning desired and the individual's skin type.

A preferred method of cosmetically or pharmaceutically treating the skin is via topical application of a safe and effective amount of the novel composition to obtain the desired amount of tanning of the skin. The amount of the composition and the frequency of topical application to the skin can vary widely, depending upon the individual's desired amount of tanning for total coverage or on an as-needed basis. The method of the present invention is suitable for daily use.

It is suggested as an example that topical application range from about once per month to about once daily, preferably from about once every three weeks to about once every two weeks, most preferably about once per week. The composition is applied in an amount of from about 0.5 ml to 5 mg/cm$^2$ preferably 2 mg/cm$^2$ of skin.

The following examples further illustrate the invention, but the invention is not limited thereto.

EXAMPLE 1

The inventive composition used in the examples is provided herein below.

| TRADE NAME | CTFA NAME | PERCENT |
|---|---|---|
| Polyolprepolymer-2 | PPG-12/SMDI Copolymer | 0.5000% |
| Arlacel 165 | Glyceryl Stearate/PEG-100 Stearate | 2.5000% |
| Silicone 200 | Dimethicone | 6.5000% |
| Cetiol LC | Coco-Caprylate/Caprate | 1.5000% |
| Wikenol 161 | Dioctyl Adipate/Octyl Stearate/Octyl Palmitate | 1.5000% |
| Propyl Paraben NF | Propylparaben | 0.1000% |
| Butyl Paraben NF | Butylparaben | 0.1000% |
| Montanov 68 | Cetearyl Alcohol/Cetearyl Glucoside | 3.0000% |
| BHT | BHT | 0.5000% |
| Purac 90 Hipure, USP | Lactic Acid | 0.0300% |
| Deionized Water | Purified Water | 54.3190% |
| Butyl Paraben NF | Butylparaben | 0.05000% |
| 1,3 Butylene glycol | Butylene glycol | 3.00000% |
| Methyl Paraben NF | Methylparaben | 0.35000% |
| Propyl Paraben NF | Propylparaben | 0.05000% |
| Methocel K4M (2% Aq. Dispersion) | Cellulose ether | 2.00000% |
| Dihydroxyacetone | Dihydroxyacetone | 3.00000% |
| Deionized Water | Purified Water | 13.0000% |
| Sucrose, Ultra Pure | Sucrose | 1.00000% |
| D-Fructose, FCC Grade | Fructose | 1.00000% |
| D-Glucose, Anhydrous (Biotech Grade) | Glucose | 1.00000% |
| Blend 338/REF 2805 | Coriander/Lavender/Cardamom/Sage | 0.00100% |
| Merosphere | URA Liposome | 3.00000% |
| Hydrolite ®-5 | Pentylene Glycol | 5.00000% |

EXAMPLE 2

A clinical study is designed to investigate the onset, intensity and tonality of self-tanning with a formulation containing Hydrolite®-5 (pentylene glycol) which is a pro-penetrant and merospheres (URA liposomes). The following materials are tested:
1. Control, DHA nanoemulsion based cream containing 3% DHA
2. 3% DHA alone
3. 3% DHA and 5% Hydrolite®-5
4. 3% DHA and 3% Merospheres
5. 3% DHA; 5% Hydrolite®-5; and 3% Merospheres
Procedure A total of twenty nine panelists participate in the study. The panel is divided into four groups of 7-8 corresponding to the four DHA materials. The panelists apply the "control" formulation containing the nanoemulsion on the right arm and the assigned DHA material on the other arm. For each panelist exact amounts (800 µl each) of the test materials are dispensed on the forearms and blended in by the panelists. Color measurements are obtained with the Chromameter before treatment and after 30 minutes, 1 hour, 2 hour, 4 hours and 24 hours.

Decrease in reflectance and increase in red coloration and yellow coloration ($\Delta L^*$, $\Delta a^*$ and $\Delta b^*$ values) obtained from the Chromameter are calculated as compared to baseline skin color. Total color change $\Delta E^*$ is calculated for each time point as follows:

$$\Delta E^* = \sqrt{(\Delta L^*)^2 + (\Delta a^*)^2 + (\Delta b^*)^2}$$

For assessing the tonality, Chroma ($\Delta C^*$) is calculated and plotted against reflectance ($\Delta L^*$ values) within the "Natural Universe of Tan". This Natural Universe is the range of color of tan obtained by multiple or single exposures to the sun. Chroma is calculated as follows:

$$\Delta C^* = \sqrt{(\Delta a^*)^2 + (\Delta b^*)^2}$$

Red values ($\Delta a^*$) are plotted against yellow coloration ($\Delta b^*$ values) within the "Natural Universe of Color" which exhibits the range of coloration from a suntan.

Results

Generally, there is a decrease in skin reflectance and an increase in skin redness and yellow coloration, due to the tanning effect of self action tanning products. As observed in FIG. 1, Formulation 2 containing DHA alone exhibits virtually the same effect as the control. Tan is visually discernable ($\Delta E \geq 1.5$) after 2 hours of treatment. Addition of Hydrolite®-5 in Formulation 3 results in increased onset and intensity of tan. Color is visible after one hour of treatment and continues to increase for 4 hours. After 24 hours there is a slight reduction in color. Addition of Merospheres in Formulation 4 does not change the onset of tan; however, the intensity of tan increases gradually and continues to increase for 24 hours. Formulation 5 containing both the Merospheres and Hydrolite®-5 exhibits an early onset of tan which increases considerably in four hours. Formulation 5 exhibits the darkest tan at the 4 hour time point after which there is a slight reduction in the tan at the 24 hour time point.

Figure 2:
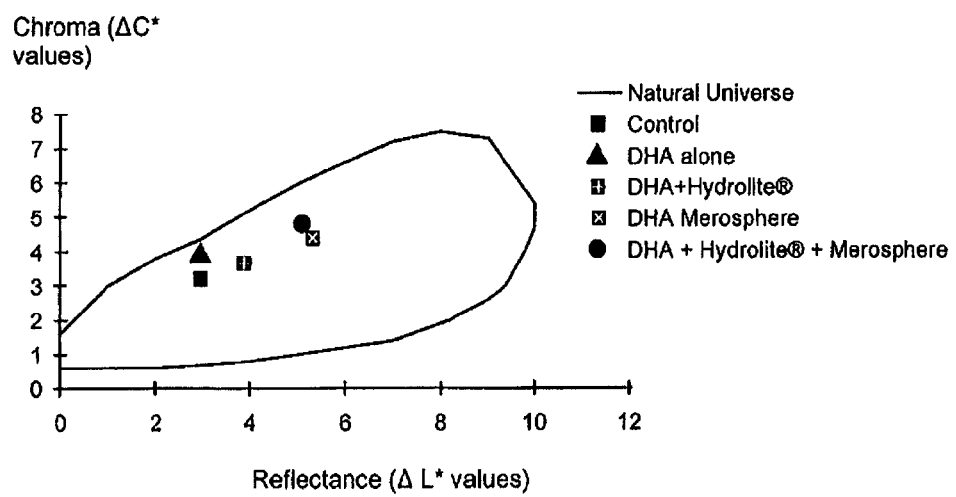
FIG. 2 Graphical depiction of the Tonality of Selftan with DHA and Ursolic Acid in Merospheres and/or Hydrolite® in Natural Universe of Tan.
Figure 3:
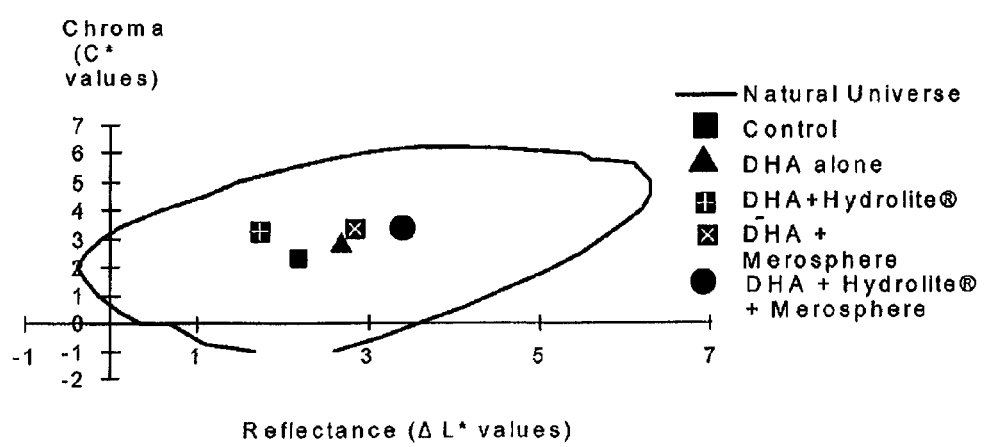
FIG. 3 Graphical depiction of the Tonality of Selftan with DHA and Ursolic Acid in Merospheres and/or Hydrolite® in Natural Universe of Color.

FIGS. 2 and 3 show the tonality of the tested formulations at the 24 hour time point plotted in the Natural Universe of Tan and color. This Universe represents the tonality of a suntan. The tonality of all the formulations are within the Natural Universe of Tan (FIG. 2). Further observation of color in the Natural Universe of Color (FIG. 3) shows that although all formulations are within this natural universe, the skin color falls more in the red coloration than observed historically for sunless tanning.

CONCLUSION

Based on the confines and conditions of this study, addition of Merospheres and Hydrolite®-5 improves the self-tanning effect of 3% DHA on skin. The formulations containing Hydrolite®-5 exhibits a tan that is visually observable within one hour of treatment. Tonality of all formulations are within the Natural Universe of Tan and Natural of Color.

EXAMPLE 3

A clinical study is designed to investigate the intensity and tonality of self-tanning with a formulation containing different combinations of merospheres, empty liposomes and ursolic acid. The following materials are tested:
1. DHA-3% and Vegetable derived Merosphere V containing ursolic acid 3%
2. DHA-3% and Cholesterol derived Merosphere containing ursolic acid 3%
3. DHA-3% and Cholesterol derived Merosphere R containing ursolic acid 3%
4. Control: DHA-3% and No Merosphere
Procedure A total of twenty-two panelists participate in the study. The panel is divided in three groups of 7-8 corresponding to the first three test materials. The panelists apply the "control" Formulation 4 containing 3% DHA and no merospheres on the right arm and the assigned test material on the other arm.

For each panelist exact amounts (800 µl each) of the test materials are dispensed on the forearms and blended in by the panelists. Color measurements are obtained with the Chromameter before treatment and 5 hours and 24 hours. Decrease in reflectance and increase in red coloration and yellow coloration ($\Delta L^*$, $\Delta a^*$ and $\Delta b^*$ values) obtained from the Chromameter are calculated as compared to baseline skin color. Total color change $\Delta E^*$ was calculated for each time point as follows:

$$\Delta E^* = V(\Delta L^*)^2 + (\Delta a^*)^2 + (\Delta b^*)^2$$

For assessing the tonality, Chroma ($\Delta C^*$) was calculated and plotted against reflectance ($\Delta L^*$ values) within the "Natural Universe of Tan". This Natural Universe is the range of color of tan obtained by multiple or single exposures to the sun. Chroma is calculated as follows:

$$\Delta C^* = V(\Delta a^*)^2 + (\Delta b^*)^2$$

Red values ($\Delta a^*$) are plotted against yellow coloration ($\Delta b^*$ values) within the "Natural Universe of Color" which exhibits the range of coloration from a suntan.

Results

Figure 4:
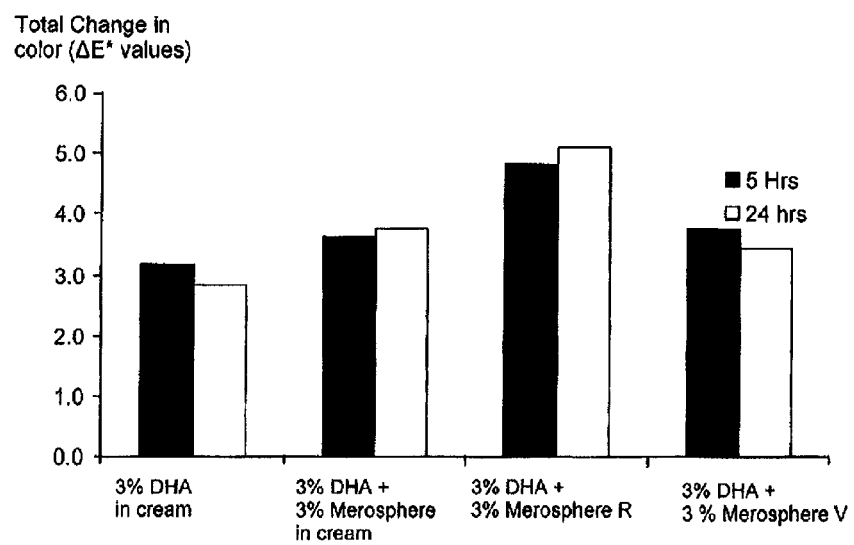
FIG. 4 Graphical depiction of the Effect of DHA and different types of Merospheres.

Referring to FIG. 4 herein, there is a decrease in skin reflectance and an increase in skin redness and yellow coloration, due to the tanning effect of self action tanning products. Furthermore, addition of vegetable derived merospheres in Formulation 1 improves the self-tanning effect of 3% DHA formulation. The cholesterol derived Formulations 2 and 3 exhibit the darkest tan on skin. In the tested Formulations, there is also an improvement in skin color with the addition of cholesterol derived merospheres.

Figure 5:
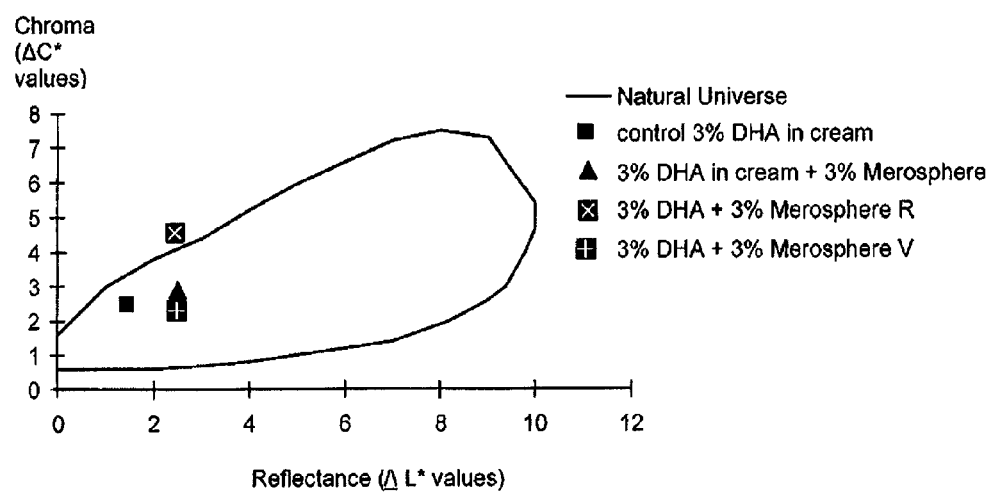
FIG. 5 Graphical depiction of the Tonality of DHA and different types of Merospheres in the Natural Universe of Tan.
Figure 6:
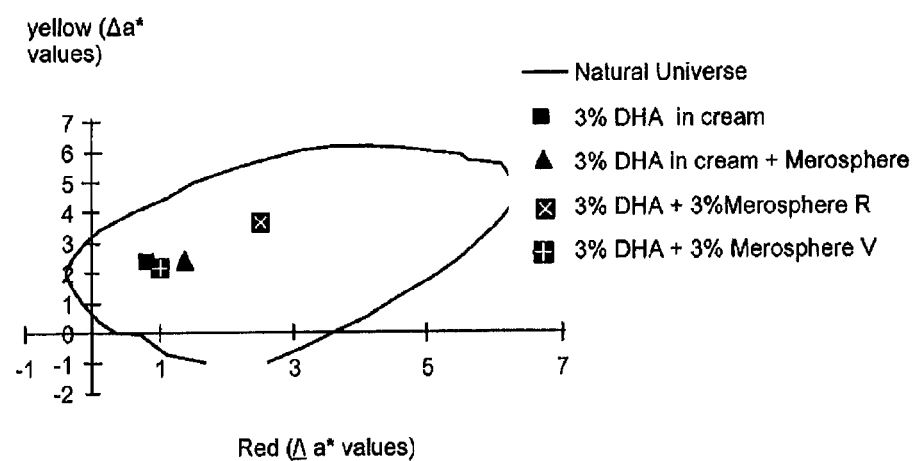
FIG. 6 Graphical depiction of the Tonality of DHA and different types of Merospheres in the Natural Universe of Color.

FIGS. 5 and 6 exhibit the tonality of the formulations at the 24 hour time point plotted in the Natural Universe of Tan and Color. This universe represents the tonality of a suntan. The tonality of all the formulations are within the Natural Universe of Tan (FIG. 5). Further observation of color in the Natural Universe of Color (FIG. 6) shows that although all formulations are within this natural universe, the DHA formulation containing the cholesterol derived merospheres exhibit the strongest color.

Conclusions

Based on the confines and conditions of this study, addition of vegetable derived and cholesterol derived Merospheres improve the self-tanning effect of 3% DHA on skin. The cholesterol derived merospheres exhibits the most improvement in self-tanning effect.

Although tonality of all formulations are within the Natural Universe of tan and color, the DHA formulations containing the cholesterol derived merospheres exhibit the strongest color.

EXAMPLE 4

This clinical study is designed to investigate the intensity and tonality of self-tanning with a formulation containing different combination of merospheres, empty liposomes and ursolic acid. The following materials are tested:

1. Control: 3% DHA, 5% Pentylene Glycol
2. 3% DHA, 5% Pentylene Glycol/Empty Liposome
3. 3% DHA, 5% Pentylene Glycol/0.05% Ursolic Acid
4. 3% DHA, 5% Pentylene Glycol/3.6% Oleanoline DPG (Olive Leaf Extract)
5. 3% DHA, 5% Pentylene Glycol/Empty Liposome/ 0.05% (Ursolic Acid)
6. 3% DHA, 5% Pentylene Glycol/3% Merosphere.
7. 7% DHA; Sunless Super Tan Procedure A total of forty-three panelists participate in the study. The panel is divided in seven groups of 7-8 corresponding to the seven test materials. The panelists apply the "control" formulation containing 3% DHA-PG on the right arm and the assigned test material on the other arm. For each panelist exact amounts (800 µl each) of the test materials are dispensed on the forearms and blended in by the panelists. Color measurements are obtained with the Chromameter before treatment and 5 hours and 24 hours.

Decrease in reflectance and increase in red coloration and yellow coloration ($\Delta L^*$, $\Delta a^*$ and $\Delta b^*$ values) obtained from the Chromameter are calculated as compared to baseline skin color. Total color change $\Delta E^*$ is calculated for each time point as follows:

$$\Delta E = V(\Delta L^*)^2 + (\Delta a^*)^2 + (\Delta b^*)^2$$

For assessing the tonality, Chroma ($\Delta C^*$) is calculated and plotted against reflectance ($\Delta L^*$ values) within the "Natural Universe of Tan". This Natural Universe is the range of color of tan obtained by multiple or single exposures to the sun. Chroma is calculated as follows:

$$\Delta C^* = V(\Delta a^*)^2 + (\Delta b^*)^2$$

Red values ($\Delta a^*$) were plotted against yellow coloration ($\Delta b^*$ values) within the "Natural Universe of Color" which exhibits the range of coloration from a suntan.

Results

Figure 7:
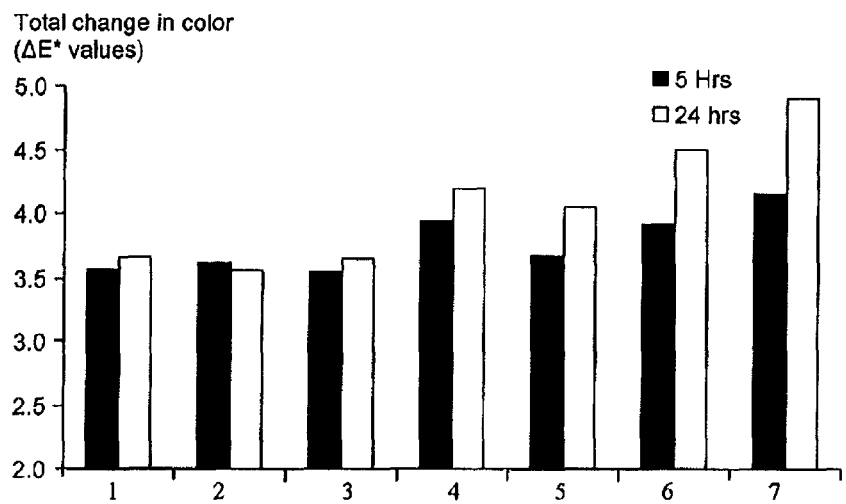
FIG. 7 Graphical depiction of the Self-tanning Effect of Ursolic Acid, Merospheres and Penetration Enhancers.

Turning to the Figures, there is a decrease in skin reflectance and an increase in skin redness and yellow coloration, due to the tanning effect of self action tanning products. As observed in FIG. 7, neither addition of empty liposomes nor ursolic acid alone changes the self-tanning effect of 3% DHA formulation. A combination of empty liposomes and ursolic acid slightly improve the sunless tanning effect of 3% DHA. Merospheres which containing ursolic acid exhibit the darkest sunless tan on skin. The Olive Leaf Extract also slightly improves the self-tanning effect of 3% DHA.

Figure 8:
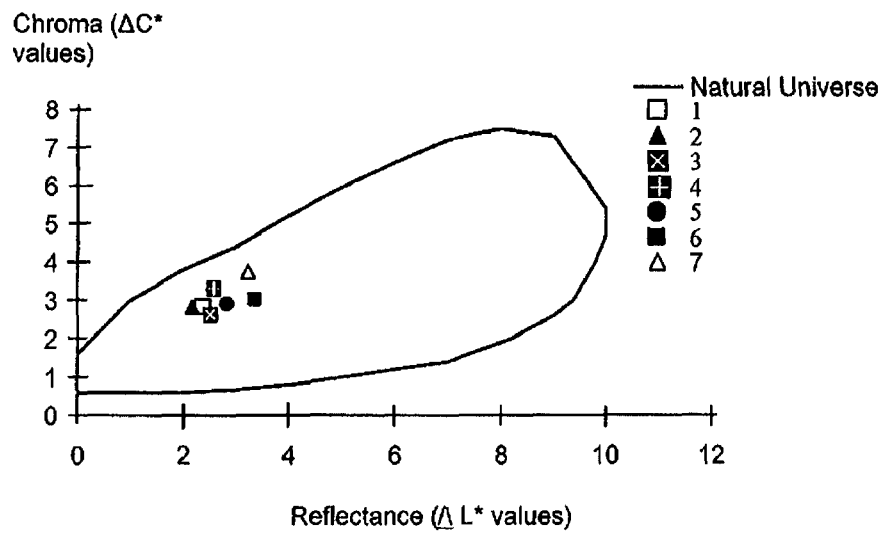
FIG. 8 Graphical depiction of the Tonality of Ursolic Acid, Merospheres and Penetration Enhancers in the Natural Universe of Tan.
Figure 9:
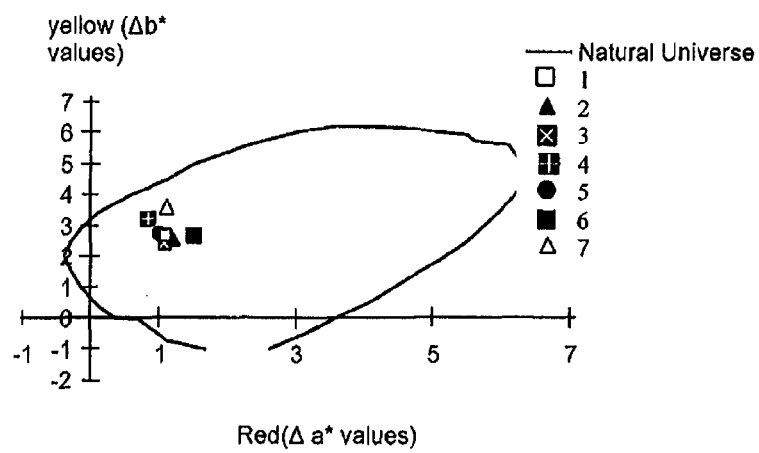
FIG. 9 Graphical depiction of the Tonality of Ursolic Acid, Merospheres and Penetration Enhancers in the Natural Universe of Tan.

FIGS. 8 and 9 depict the tonality of the formulations at the 24 hour time point plotted in the Natural Universe of Tan and Color. This universe represents the tonality of a suntan. The tonality of all the tested formulations are within the Natural Universe of Tan (FIG. 8).

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A topical self-tanning skin composition comprising:
   liposome encapsulated ursolic acid;
   self-tanning agent; and
   a cosmetically acceptable carrier.

2. The composition of claim 1 wherein the ursolic acid is present in the liposome from 0.001% to 0.9% by weight of the liposome.

3. The composition of claim 1 wherein the self-tanning agent is dihydroxyacetone and is encapsulated in a liposome.

4. The composition of claim 1 further comprising a penetration enhancer selected from the group consisting of C12-15 Alkyl Benzoate, pentylene glycol, polyethylene glycol, ethoxydiglycol, dimethylsulfoxide, sodium lauryl sulfate, polysorbate-polyethylenesorbitan-monolaurate, lecithin and mixtures thereof.

5. The composition of claim 1 further comprising pentylene glycol.

6. A method of tanning the skin comprising applying to the skin a composition comprising a liposome encapsulated ursolic acid, dihydroxyacetone, and a cosmetically acceptable carrier.

7. The method of claim 6 wherein ursolic acid is present in the liposome from 0.001% to 0.9% by weight of the liposome.

8. The method of claim 6 wherein the dihydroxyacetone is encapsulated in a liposome.

9. The method of claim 6 wherein the composition further comprises a penetration enhancer selected from the group consisting of C12-15 Alkyl Benzoate, pentylene glycol, polyethylene glycol, ethoxydiglycol, dimethylsulfoxide, sodium lauryl sulfate, polysorbate-polyethylenesorbitan-monolaurate, lecithin and mixtures thereof.

10. The method of claim 6 further comprising pentylene glycol.

11. A method of tanning the skin comprising applying to the skin a composition comprising a liposome encapsulated ursolic acid, liposome encapsulated dihydroxyacetone, and a cosmetically acceptable carrier.

12. The method of claim 11 wherein the liposome encapsulated ursolic acid is present from 0.001% to 0.9 % by weight of the composition.

13. The method of claim 11 wherein the composition further comprises a penetration enhancer selected from the group consisting of C12-15 Alkyl Benzoate, pentylene glycol, polyethylene glycol, ethoxydiglycol, dimethylsulfoxide, sodium lauryl sulfate, polysorbate-polyethylenesorbitan-monolaurate, lecithin and mixtures thereof.

14. The method of claim 11 wherein the composition further comprises pentylene glycol.

* * * * *